United States Patent [19]

Lieberman et al.

[11] Patent Number: 4,752,464

[45] Date of Patent: Jun. 21, 1988

[54] TREATMENT OF ARTHRITIS, INCLUDING RHEUMATOID ARTHRITIS, WITH RADIOACTIVE ISOTOPES

[75] Inventors: Ephraim Lieberman, Suffern; Maurice E. Bordoni, Westtown; Alfred K. Thornton, New Hampton, all of N.Y.

[73] Assignee: Cadema Medical Products, Inc., Middletown, N.Y.

[21] Appl. No.: 742,402

[22] Filed: Jun. 7, 1985

[51] Int. Cl.$^4$ .......................... A61K 43/00; A61N 5/10
[52] U.S. Cl. .......................... 424/1.1; 128/1.1
[58] Field of Search .......................... 424/1.1; 534/10; 128/1.1; 423/249

[56] References Cited

U.S. PATENT DOCUMENTS 3,961,038 6/1976 Benes .................................. 424/1.1

FOREIGN PATENT DOCUMENTS 176288 4/1986 European Pat. Off. ............. 424/1.1

OTHER PUBLICATIONS

Hackh's Chemical Dictionary, 4th Edition, McGraw-Hill, p. 168 (1969).
Singh et al, Indian J. Radiology, 25(4), Nov. 1971.
Hnatowich et al, CA 88:148276, 1978.
Rebut-Bonneton et al, CA 84:161223, 1976.
Bertrand et al, CA 87:1863, 1977.
Bard et al, CA 99:136168, 1983.

Primary Examiner—John F. Terapane
Assistant Examiner—J. E. Thomas
Attorney, Agent, or Firm—Leonard Bloom

[57] ABSTRACT

Treatment of rheumatoid arthritis by administering a radioactive compound to the inflamed synovium of the articular joint. The compound comprises an aggregate suspension having a radionuclide entrapped therein. The aggregate suspension is a ferric or aluminum hydroxide aggregate, and the radionuclide is selected from the group consisting of $^{166}$Holmium, $^{153}$Samarium, $^{175}$Ytterbium, $^{169}$Erbium, and $^{176m}$Lutetium. The radionuclide may also consist of $^{51}$Chromium. Suitable leakage inhibitors or agents to reduce leakage of the radionuclide from the articular joint is included as part of the chemical composition of the final drug form.

4 Claims, No Drawings

2

TREATMENT OF ARTHRITIS, INCLUDING RHEUMATOID ARTHRITIS, WITH RADIOACTIVE ISOTOPES

FIELD OF THE INVENTION

The present invention relates to a radioactive compound, the methods for the preparation thereof and a method for the treatment of arthritis and, more particularly, radioactive compounds and a method for the treatment of rheumatoid arthritis.

BACKGROUND OF THE INVENTION

Arthritic disorders are the second leading cause of losses in time and earnings in the United States. Approximately nine percent (9%) of all arthritis sufferers are afflicted with a type of arthritis known as rheumatoid arthritis. Of these, approximately fifty-six percent (56%) ultimately will have involvement of the knee joint, eighty-seven percent (87%) of the hand joint and somewhat smaller percentages will have involvement of other joints such as the ankle, elbow and shoulder.

The source of disability for the sufferer of rheumatoid arthritis is an inflammatory response, of unknown origin, in the synovium, or lining, of the afflicted joint. This chronic inflammation, or synovitis, leads to pannus formation and, eventually, enzymatic destruction of the joint cartilage.

Presently, the primary method of treating rheumatoid arthritis is by use of compounds directed at blocking the inflammatory process. Unfortunately, these attempts are quite often unsuccessful. In such instances, the primary alternative is the surgical excision of the inflamed synovium in a procedure known as surgical synovectomy. While, in many cases, this procedure proves to temporarily arrest the disease, it also has a significant number of drawbacks and limitations. Among these are limitations on just how much of the inflamed synovium can be surgically excised; the operation itself; the risks and dangers inherent therein; and the required lengthy recovery period, much of which is spent in the hospital.

In order to overcome these problems, attempts (albeit unsuccessful) have been made with radiation synovectomy. The prior art reveals that intra-articular colloidial Gold-198 ($^{198}$Au) was reported to abate inflamed synovium (Fellinger, et al., 33 WEIN Z. INN, Med. 351, 1951). However, this procedure did not gain acceptance until the report of Ansell, et al., 22 Ann. Rheum. Dis. 435 (1963). Unfortunately, due to $^{198}$Au emission of a high energy photon (gamma emission) these attempts proved unsatisfactory. The presence of the aforementioned emission poses dangers to the patient by increasing the whole body dose, thereby exposing healthy tissue to the destructive radioactivity, and poses substantial difficulties with radiation protection for hospital personnel.

Other radionuclides have also been unsuccessfully utilized in radiation synovectomy. These include Erbium-169 ($^{169}$Er) Menkes, et al., 36 Ann. Rheum. Dis. 254 (1977); Rhenium-186 ($^{186}$Re) Deckart, et al., 3 Radiobiol, Radiother 363 (1979) and DelBarre et al., 2 Nouv. Presse. Med 1372 (1973); Phosphorus-32 ($^{32}$P) Wenston, et al., 14 J. Nuc. Med 886 (1973), and Yttrium-90 ($^{90}$Y) Gumpel, et al., 48 Br. J. Radiol. 377 (1975).

Disadvantages common to each of these radionuclides proved to be their long physical half-lives and the occurence of radioleakage in significant amounts, from the affected joints. (See also Oka, et al., 17 Acta Rheum. Scand. 148 (1971) and Virkkunen, et al., 13 Acta Rheum. Scand., 1967). There exists, however, notable exceptions to these isotopic characteristics.

Currently the preferred and only suitable radionuclide in the prior art is Dysprosium-165 ($^{165}$Dy) in ferric hydroxide. Sledge, et al., 182 Clin. Ortho, and Rel. Research 37 (1984) (hereinafter referred to as "Sledge"). Sledge has found that the use of $^{165}$Dy can overcome the problems previously encountered by use of the aforementioned radionuclides in radiation synovectomy. This is because $^{165}$Dy is a beta emitter, has a maximum soft tissue penetration of approximately 5.7 mm, forms a larger colloid which reduces the effects of leakage of the injection close to the lymph nodes, and has an extremely short half-life of 2.3 hours which further reduces the effects of potential leakage.

These are qualities which the prior art has reported to be desirable when selecting an appropriate isotope for radiation synovectomy (Sledge, et al., 20 Arthritis Rheum 1334 (1977), Noble, et al., 65A J. Bone Joint Surg. 381 (1983), and Deckert and Gumpel, both supra).

While $^{165}$Dy's short half-life is a major characteristic noted by Sledge in the prior art as making it a suitable candidate for radiation synovectomy, this short half-life also proves to be its major limitation. $^{165}$Dy requires a nuclear reactor to be produced. It also must be injected within a few hours of its manufacture to be effective. As a result, its utility in radiation synovectomy is severely limited by geographical and distribution factors.

Accordingly, there remains an obvious need for an effective radioactive compound that will have both utility in radiation synovectomy and will be able to be prepared in, and distributed from, a central location using existing transportation channels.

SUMMARY OF THE INVENTION

According to this invention, certain radioactive compounds have utility in radiation synovectomy for the treatment of rheumatoid arthritis. In accordance with the teachings of this invention, such physical qualities are a relatively large particulate carrier, and a radionuclide that has beta or Auger electron emissions and not high levels of other types of energies which can damage healthy tissue. Also, in accordance with this invention, a radionuclide with a half-life long enough to permit the compound's central preparation and distribution is desirable.

The radioisotopes which we have found to exhibit the aforementioned physical properties and which are suitable for radiation synovectomy are $^{166}$Holmium, $^{153}$Samarium, $^{175}$Ytterbium, $^{169}$Erbium, and $^{176m}$Lutetium.

We believe that $^{51}$Chromium may also prove suitable. $^{51}$Cr emits low energy Auger electrons which, like beta emissions, will destroy the diseased synovium.

Chromium 51 has a longer half-life than the other species mentioned above but is a prolific producer of low energy Auger electrons due to electron capture. (100%.) This characteristic results in Chromium emitting 93 millirads of energy per disintegration. Therapeutic doses of radiation (5,000–10,000 rads) can be delivered to small localized diseased areas in man.

Because of this property, only small amounts of Chromium 51 are injected into the articular joint. If 3 mCi or 3,000 uCi were utilized and there was undue leakage as reported in earlier studies, (up to 10% of the injected dose), the Chromium leaking from the articular joint would be less than the amount of Chromium 51 presently used in vivo in studies in man to determine certain blood parameters. Thus, Chromium should be considered as a suitable radionuclide.

Accordingly, it is the primary object of this invention to provide radioactive isotopes in a form useful in the treatment of arthritis and, more particularly, useful for radiation synovectomy in the treatment of rheumatoid arthritis.

It is another object of this invention to provide methods for the treatment of arthritis and, more particularly, rheumatoid arthritis.

It is still another object to provide a radioactive compound for the treatment of arthritis, and more particularly, rheumatoid arthritis, which can be prepared at and distributed from a central location utilizing existing transportation channels.

It is yet still another object of this invention to provide a method for the preparation of a radioactive compound useful in radiation synovectomy in the treatment of rheumatoid arthritis.

These and other objects are accomplished by one or more embodiments made in accordance with the teachings of the present invention.

In one embodiment, a radioactive compound is provided and comprised of a ferric or aluminum hydroxide aggregate suspension in which one of the following radionuclides is entrapped: $^{153}$Samarium, $^{166}$Holmium, $^{175}$Ytterbium, $^{169}$Erbium, $^{51}$Chromium, and $^{176m}$Lutetium.

In another embodiment, the present invention contemplates a method for the use of radioactive compounds for the treatment of arthritis and, more particularly, rheumatoid arthritis.

In yet another embodiment, the present invention contemplates a method for the preparation of an aggregate suspension wherein a radionuclide is entrapped.

The present invention also contemplates a radioactive compound for the treatment of rheumatoid arthritis which can be prepared at, and distributed from a central location using available transportation channels.

This invention provides radioactive compounds comprised of an aggregate suspension having entrapped therein a radionuclide possessing particular physical qualities that make it appropriate to utilize when performing radiation synovectomy in the treatment of rheumatoid arthritis. The compounds utilized in the prior art are unsatisfactory in that they either have potentially harmful radioactive emissions or possess a half-life that is either too long for safe use or too short to permit its use, except within those areas in a close physical proximity to a nuclear reactor.

The radioactive compounds provided herein primarily have beta and/or Auger electron emissions. They do not have high energy gamma emissions in any abundance which would have a harmful effect on healthy tissue and hospital personnel. Finally, the isotopic compounds of this invention each have properties which minimize leakage and excess radiation while permitting the radioactive compound to be prepared as a drug at a central location for delivery of the same to hospitals, clinics and radiology centers through available transportation channels. Thereafter, the radioactive compound may conveniently be administered, when needed, to a patient in need thereof.

Preferably in the improved method of the present invention, the compound used is a ferric or aluminum hydroxide aggregate suspension containing a stabilizing matrix such as polyvinyl pyrrolidone (PVP) or large molecular polymers combined with the radioisotopes described herein.

The nature and substance of the present invention, as well as its objectives and advantages, will be more clearly perceived and fully understood by referring to the following description and claims.

DESCRIPTION OF PREFERRED EMBODIMENTS

The radioactive compounds of this invention have a particular utility in the treatment of arthritis and, more specifically, rheumatoid arthritis. They also have a particular utility in radiation synovectomy. These compounds are prepared by entrapping a suitable radionuclide within an aggregated carrier.

The preferred aggregated carrier in this practice is a ferric or aluminum hydroxide aggregate within which is entrapped a suitable radionuclide. This radionuclide may be one of the following: $^{153}$Samarium, $^{166}$Holmium, $^{109}$Ytterbium, $^{165}$Erbium, $^{51}$Chromium, and $^{176m}$Lutetium.

The radioactive ferric or aluminum hydroxide aggregate suspension useful in this practice is prepared by a method comprising irradiation of the oxide form (or some other suitable form) of the radionuclide in a nuclear reactor to obtain the desired species of the radioactive compound. Following irradiation, the radionuclide is dissolved in concentrated hydrochloric acid to produce a chloride form of the radionuclide. To this solution is then added a solution of ferric or aluminum chloride. Sodium hydroxide is then added to this solution in an amount sufficient to adjust the pH of the solution to a value of from 4 to 9. The product is an aggregated precipitate of ferric or aluminum hydroxide within which is entrapped the radionuclide utilized. This product is then sterilized by one of several methods well known in the art and tested for pyrogens by methods also well known in the art.

The radionuclide utilized must be one having the desired physical properties.

The radionuclides of this invention include $^{153}$Samarium, $^{166}$Holmium, $^{176m}$Lutetium, $^{175}$Ytterbium, $^{169}$Erbium and $^{51}$Chromium. The preferred radionuclides are $^{166}$Holmium and $^{153}$Samarium.

Holmium has a half-life of 26.9 hours which, unlike $^{165}$Dy, allows the necessary time following production in a nuclear reactor for preparation and distribution of the finished drug. $^{166}$Holmium has beta energy ranges from 0.23 to 1.8 MeV with the lower being 2% abundant and the higher energy being 85% abundant. These figures are equivalent to those of $^{165}$Dy whose beta energy ranges from 0.22 to 1.8 MeV with the lower being 0.1% abundant and the higher being 83% abundant.

$^{166}$Holmium has an 80 keV gamma photon in an abundance of 6%. Although there is a high energy gamma emission, it is less than 1% in abundance and therefore presents no real problem to either the patient or hospital personnel. Thus it is also similar in this physical quality to $^{165}$Dy which has no high energy gamma emission.

The internal conversion of $^{166}$Holmium is about 50%.

The activation cross-section of $^{166}$Holmium for thermal neutrons is 62 barns and the $^{166}$Holmium is 100% abundant. With that cross-section and $5 \times 10^{13}$ thermal neutron flux, one can produce, in one week of irradiation, 285 mCi per mg of Holmium. Calculations, well known to those skilled in the art, indicate that about 25 mCi injected into an arthritic knee articular joint will deliver approximately 10,000 rads of the synovial membrane. This compares favorable to 5 mL of $^{90}$Y required to deliver 10,000 rads. GUMPEL, supra, and doses of 270 mCi of $^{165}$Dy required to deliver the same 10,000 rads, Sledge, supra at 38.

Samarium 153 has excellent physical properties. Its half-life is 47 hours. It emits beta particles of excellent energies in the following amounts: 0.63 MeV—26% abundance, 0.70—53% abundance, 0.80—20% abundance. The internal conversion is 64% and its cross-section is 37 barns, making production of large amounts of the isotope in a nuclear reactor relatively simple and inexpensive. (It has a very low energy gamma which would not prove objectionable.) 3–5 mCi of Samarium injected into the joints of afflicted fingers in the rheumatoid arthritic patients would produce therapeutic doses of radiation. Such patients could be treated on an outpatient basis because of the quantity of Samarium utilized.

Other radionuclides of this invention of the same class as $^{166}$Holmium and $^{165}$Dy are $^{153}$Samarium, $^{169}$Erbium, and $^{175}$Ytterbium. Like $^{166}$Holmium each has beta emissions. $^{153}$Samarium has beta energy ranges from 0.679 to 0.801 MeV with the lower energy being 32% abundant and the high energy being 20% abundant. $^{169}$Erbium has beta energy ranges from 0.332 to 0.34 MeV with the lower energy being 42% abundant and the higher energy being 58% abundant. $^{175}$Ytterbium has beta ranges from 0.073 to 0.466 MeV with the lower energy being 11% abundant and the higher energy being 87% abundant. Thus it can be seen that, like $^{165}$Dy and $^{166}$Holmium, these radionuclides possess beta energy ranges and abundances that are well within the levels which are safe. With half-lives of 46.8 hours for $^{153}$Samarium and 101 hours for $^{175}$Ytterbium respectively, like $^{166}$Holmium, they make the suitable candidates for radiation synovectomy.

The resultant $^{166}$Holmium-ferric or aluminum hydroxide aggregate carrier has a size of 3–20 μm. This also compares favorably with the 3–10 μm particle size reported as effective for $^{165}$Dy-FHMA, Sledge, supra.

The $^{166}$Ho hydroxide preparation is then administered to the patient in need thereof by a method well known to those skilled in the art.

Leak inhibitors or agents used to reduce leakage of the radionuclide from the articular joint will be incorporated into the aggregate suspension. These agents could include carboxalate chelating compounds, such as ethylenediaminetetraacetic acid (EDTA) or diethylenetriaminepentaacetic acid (DTPA); in addition, inorganic hydroxides such as manganese hydroxide; or organo-metalic compounds such as oximes or citrates; or high molecular weight surface active agents such as (PVP) polyvinyl pyrrolidone; and poloxamers such as Pluronic F68.

The amount of the radioactive compound to administer as a therapeutic agent is within the skill of the practitioner. Production of the radioactive compounds of the present invention, involving use of a nuclear reactor, is relatively simple and inexpensive. The length of their half-lives simplify distribution and logistic problems, as well as problems associated with the ultimate disposal of the compounds, thereby facilitating the widespread commercialization of this invention.

Thus, this invention provides novel radioactive compounds; a method for the preparation of such compounds; and a method that is useful in the treatment of arthritis and, more particularly, rheumatoid arthritis, and for alleviating, to some extent, the pain and suffering associated therewith.

While specific embodiments of the present invention have been shown and described to illustrate inventive principles, it is to be understood that such showing and description have been offered only by way of example and not limiting. Protection by Letters Patent of this invention in all its aspects as the same are set forth in the appended claims is sought to the broadest extent that the prior art allows.

What is claimed is:

1. A radioactive composition for the treatment of arthritis comprising, in combination, a ferric hydroxide or aluminum hydroxide aggregate suspension having a particle size of 3 to 20 microns, wherein a radionuclide is entrapped, said radionuclide being $^{166}$Holmium.

2. A method for the treatment of arthritis comprising administering an effective amount of the radioactive composition of claim 1 to the inflamed synovium of the particular joint of a mammal body in need of such treatment.

3. A radioactive composition consisting essentially of, in combination, a ferric hydroxide aggregate suspension having a particle size substantially in a range of 3–20 microns, wherein a radionuclide is entrapped, said radionuclide being $^{166}$Holmium.

4. A radioactive composition for the treatment of rheumatoid arthritis comprising, in combination, a ferric hydroxide aggregate suspension having a particle size substantially in a range of 3–20 microns, wherein a radionuclide is entrapped, said radionuclide being $^{166}$Holmium.

* * * * *